US012642880B2

(12) United States Patent
Bebon et al.

(10) Patent No.: US 12,642,880 B2
(45) Date of Patent: Jun. 2, 2026

(54) AIR TREATMENT UNIT FOR VENTILATION EQUIPMENT

(71) Applicant: ALSTOM Transport SA, St Ouen sur Seine (FR)

(72) Inventors: Dominique Bebon, Weyersheim (FR); Helian Randrianarisoa, Goxwiller (FR); Alexandre Xolin, Molsheim (FR)

(73) Assignee: ALSTOM Transport SA, St Ouen sur Seine (FR)

( * ) Notice: Subject to any disclaimer, the term of this patent is extended or adjusted under 35 U.S.C. 154(b) by 354 days.

(21) Appl. No.: 18/142,007

(22) Filed: May 1, 2023

(65) Prior Publication Data

US 2023/0355826 A1 Nov. 9, 2023

(30) Foreign Application Priority Data

May 4, 2022 (FR) ...................................... 2204236

(51) Int. Cl.
*A61L 9/20* (2006.01)
*B60H 3/00* (2006.01)

(52) U.S. Cl.
CPC .............. *A61L 9/20* (2013.01); *B60H 3/0078* (2013.01); *A61L 2209/12* (2013.01); *A61L 2209/16* (2013.01)

(58) Field of Classification Search
None
See application file for complete search history.

(56) References Cited

U.S. PATENT DOCUMENTS

2010/0196222 A1 8/2010 Kosugi et al.

FOREIGN PATENT DOCUMENTS

| CA | 2435878 | C | * | 9/2007 | ............... A61L 9/18 |
|----|---------|---|---|--------|--------|
| EP | 4 215 219 | | | 7/2023 | |
| JP | 3 390429 | | | 3/2003 | |
| JP | 3390429 | B1 | * | 3/2003 | |
| KR | 102 211 993 | | | 2/2021 | |
| WO | 03/086792 | | | 10/2003 | |
| WO | 2016/085171 | | | 6/2016 | |
| WO | 2022/234875 | | | 11/2022 | |

OTHER PUBLICATIONS

International Search Report dated Dec. 9, 2022.

* cited by examiner

*Primary Examiner* — Andrew Smyth
(74) *Attorney, Agent, or Firm* — IPSILON USA, LLP

(57) ABSTRACT

An air treatment unit (1) produced in the form of a cartridge (2) is provided, which is configured to be positioned on at least part of the air circulation path in ventilation equipment. This treatment unit (1) has an interior volume (21) which is associated with at least one input orifice (3) and at least one output orifice (4) positioned at the ends of an air circulation path. At least part of the interior surface of the volume (21) is equipped with at least one light-emission source (5) with a wavelength of between 100 nm and 400 nm, designed to radiate towards the interior of the volume of the unit (1) at one section at least of the air circulation path in the interior of the volume of the unit (1).

7 Claims, 2 Drawing Sheets

AIR TREATMENT UNIT FOR VENTILATION EQUIPMENT

RELATED APPLICATION

This application claims the benefit of priority from French Patent Application No. 22 04236, filed on May 4, 2022, the entirety of which is incorproated by reference.

FIELD OF THE INVENTION

The present invention relates to the field of ventilation devices for vehicles, and more particularly to the field of ventilation devices which permit treatment of the ventilated air.

BACKGROUND

Public transport vehicles form substantially confined structures, in the interior of which the users are forced to encounter one another, in particular within the context of intermittent densities of population which can be particularly substantial, particularly during peak periods. This peak and the flow of passengers in the interior of the vehicle, with a certain amount of overcrowding, create a site which is favourable to the circulation and transmission of viruses and germs.

Although the doors of the vehicle are opened regularly at stops in order for passengers to get in and out, these openings of the doors are carried out during limited periods which do not make it possible to introduce a substantial volume of fresh air, and therefore renew sufficiently the air in the passenger space of the vehicle. Thus, in order to improve this renewal, ventilation mechanisms are incorporated in the vehicle such as to permit firstly mixing of the interior air of the vehicle, and secondly importing of air into the interior of the passenger space from the exterior of the vehicle. However, the ventilation of the vehicle is generally not sufficient for the volume of air introduced into the passenger space to be sufficient for rapid renewal of the interior air of the passenger space. Consequently, in the presence of viruses and/or germs which can persist in a closed environment and at temperate temperatures, ventilation mechanisms of this type are not able to reduce, or prevent, contamination of the passengers via respiratory channels.

OBJECTS AND SUMMARY

The objective of the present invention is to eliminate these disadvantages by proposing a solution which makes it possible to limit, or prevent, the risks of contamination of passengers of the vehicle by a germ and/or a virus which may be in suspension in the atmosphere, while being able to be adapted to, and/or incorporated in, existing ventilation mechanisms of vehicles.

The invention relates to an air treatment unit produced in the form of a cartridge which is configured to be positioned on at least part of the air circulation path in ventilation equipment, this treatment unit comprising an interior volume which is associated with at least one input orifice and one output orifice which are positioned at the ends of an air circulation path, characterised in that at least part of the interior surface of the volume is equipped with at least one light-emission source with a wavelength of between 100 nm and 400 nm, designed to radiate towards the interior of the volume of the unit at one section at least of the air circulation path in the interior of the volume of the unit.

The invention also concerns a ventilation device which incorporates at least one treatment unit according to the invention.

BRIEF DESCRIPTION OF THE DRAWINGS

The invention will be better understood, thanks to the following description relating to preferred embodiments, which are provided by way of non-limiting examples, and are explained with reference to the appended schematic drawings, in which.

DETAILED DESCRIPTION

Figure 1:
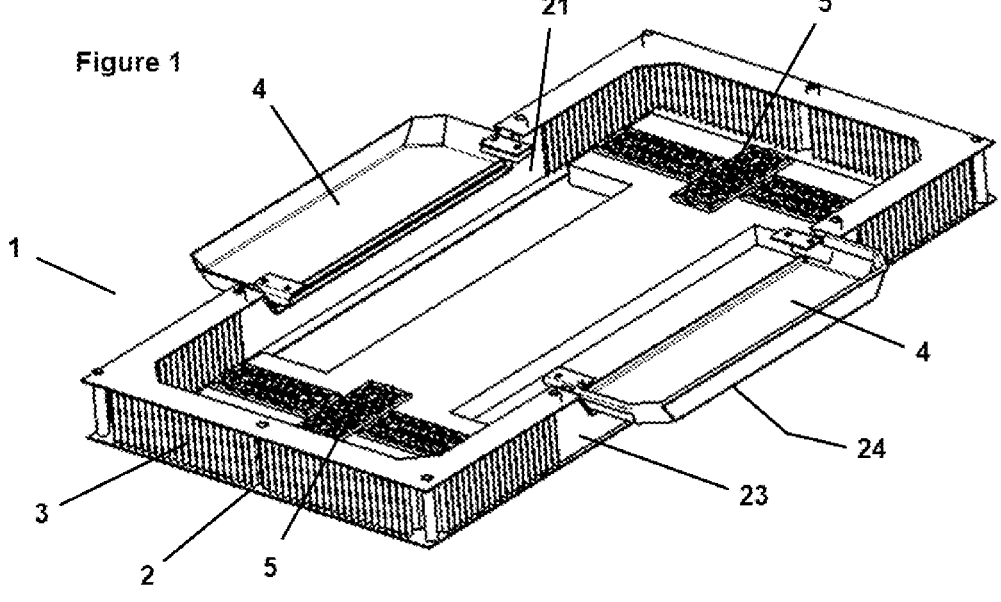
FIG. 1 represents a schematic illustration of an example of an air treatment unit according to the invention.
Figure 2:
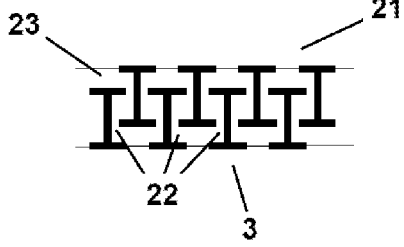
FIG. 2 represents a schematic illustration of an example of an arrangement of baffles at a peripheral frame of an example of an air treatment unit according to the invention.
Figure 3:
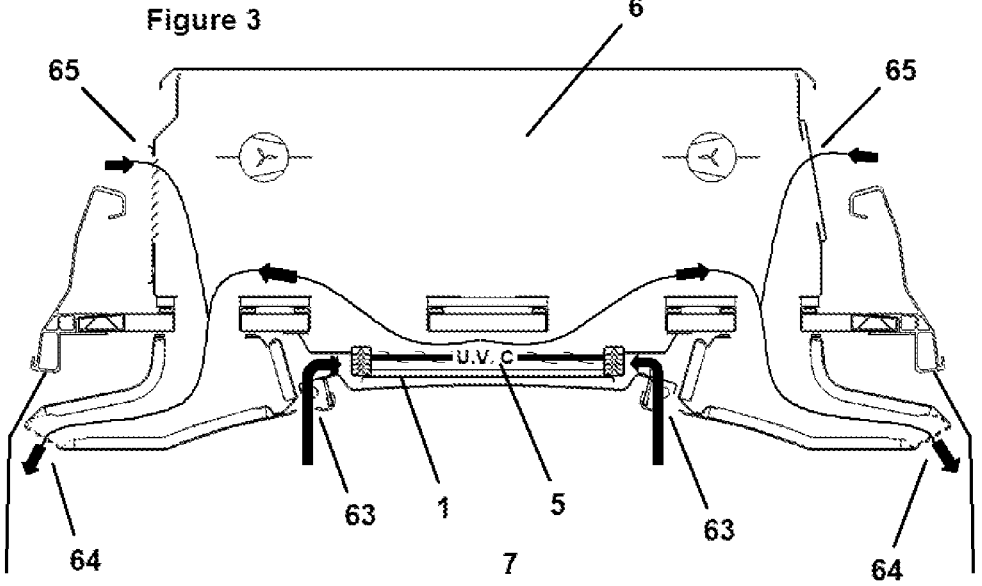
FIG. 3 represents a schematic illustration of an example of a ventilation device incorporating an air treatment unit according to the invention.

The invention relates to an air treatment unit 1 produced in the form of a cartridge 2, which is configured to be positioned on at least part of the air circulation path in ventilation equipment, this treatment unit 1 comprising an interior volume 21 which is associated with at least one input orifice 3 and at least one output orifice 4 positioned at the ends of an air circulation path, characterised in that at least part of the interior surface of the volume 21 is equipped with at least one light-emission source 5 with a wavelength of between 100 nm and 400 nm, designed to radiate towards the interior of the volume of the unit 1 at one section at least of the air circulation path in the interior of the volume of the unit 1.

The treatment air unit 1 according to the invention thus provides a treatment duct through which a volume of air is circulated, such that this volume of air has passing through it at least part of the radiation of the light-emission source 5. This light-emission source 5 is specifically selected to diffuse radiation with a wavelength of between 100 nm and 400 nm, i.e. radiation of the ultraviolet type, which has germicide and virucide properties. Preferably, the ultraviolet radiation involves UV of type C, and/or radiation with a wavelength of between 250 and 270 nm. Radiation of the ultraviolet type can be absorbed by the nucleic acids, RNA and DNA, which constitute the genetic material of the germs and viruses, such that this genetic material can be degraded. Also, the germs and viruses in suspension in the air which circulates in the treatment unit 1 can have their genetic material degraded by the ultraviolet radiation, and thus be destroyed. Germs and viruses can thus be eliminated from the flow of air at an output 4 of the treatment unit 1. Depending on the length of the course of the flow of air through the ultraviolet radiation and depending on the intensity of this radiation, the degradation of the genetic material of the germs and viruses in suspension will be able to be more accentuated.

It should be pointed out that the treatment unit 1 according to the invention is without a specifically dedicated ventilation mechanism. Since this treatment unit 1 is intended to be incorporated in ventilation equipment, it is configured to take advantage of the flow of air generated by the ventilation equipment in order to act on the germs and viruses in suspension in the air in circulation, without any ventilation mechanism specific to the treatment unit 1 being necessary. This lack of an additional ventilation mechanism incorporated in the treatment unit 1 also makes it possible to limit the volume of operating sound associated with the motorisation of the circulation of the air.

According to an example of a structure relating to a variant of the invention, the air treatment unit 1 is characterised in that at least part of the interior surface of the interior volume 21 is produced in the form of a surface which is suitable for reflection of at least part of the radiation with a wavelength of between 100 nm and 400 nm, such that this radiation converges at one section at least of the air circulation path in the interior of the volume 21 of the unit 1. The positioning of reflective surfaces in the interior volume 21 of the air treatment unit 1 makes it possible to optimise the distribution of the radiation in the interior of the volume 21 of the unit 1 based on a single source of radiation. In fact, the reflection of the radiation in the interior of the interior volume makes it possible to limit the energy losses by concentrating the radiation on the air flow circuit in the interior of the treatment unit 1. Thanks to the reflective surfaces, a single ray can thus pass through the air flow in the processing unit 1 several times, such that the chances impact of a germ and a virus in suspension in the air, and thus the effect of the radiation on the genetic material thereof, are increased. In the interior volume 21 of the unit 1, the efficiency of the radiation provided by a single light-emission source 5 for the treatment of the flow of air in circulation is thus optimised. The different reflective surfaces of the interior volume 21 of the air treatment unit 1 can correspond to flat surfaces, or, alternatively, to surfaces with convexity or concavity. In a complementary manner, these surfaces can be produced by means of a combination of flat and/or convex and/or concave portions of surface. According to an example of a structure, these reflective surfaces are produced in the form of paint or a covering, for example of the mirror or chrome or also aluminium type.

According to an example of a structure relating to another variant embodiment of the invention, which can be combined with the different preceding variant embodiments, the air treatment unit 1 is characterised in that the air circulation path in the interior of the volume of the unit 1 comprises at least one baffle 22 positioned in the interior volume 21, such that no ray obtained from the at least one light-emission source 5 can pass through the at least one input orifice 3 and/or the at least one output orifice 4 of the treatment unit 1. The baffle 22 is positioned in the interior of the treatment unit 1, such that one of its walls can prevent emission of light with a wavelength of between 100 nm and 400 nm towards the exterior of the air treatment unit 1. Thus, the effect of the UV radiation of the sources of emission 5 of the treatment unit 1 on nucleic acids is strictly circumscribed within the interior volume 21. Only the elements which are present in the interior volume 21 of the treatment unit 1, in particular in suspension in the air flow in circulation, are subjected to the UV radiation. The risk of an effect of this UV radiation on the exterior of the treatment unit is avoided. Thus, the incorporation of a treatment unit 1 according to the invention in a vehicle, in particular in an environment which is accessible to passengers or users, can operate without any UV radiation emitted in the interior of the treatment unit 1 reaching one of the passengers or users. According to a preferred structure, the baffle 22 is positioned between firstly the at least one light-emission source 5, and secondly the at least one input orifice 3 and/or the at least one output orifice 4 of the treatment unit 1. By way of example, at least one of the walls of the baffle 22 is positioned such as to shield the at least one input orifice 3 and/or the at least one output orifice 4 from one or more points of radiation of the light-emission source 5. According to another example which relates to a specific aspect of this structural variant, the air treatment unit 1 comprises a plurality of baffles 22, the distribution and positioning of which in the interior volume of the treatment unit 1 make it possible to use a combination of a plurality of the respective walls of these baffles 22 such as to shield the at least one input orifice 3 and/or the at least one output orifice 4 from one or more points of radiation of the light-emission source 5. According to another example which relates to another specific aspect of this structural variant, at least one surface of this baffle can also be suitable for reflection of at least part of the radiation with a wavelength of between 100 nm and 400 nm, such as to optimise the retention of the radiation in the interior of the treatment unit 1.

The incorporation of one or a plurality of baffles 22 in the interior of the treatment unit 1 also has the advantage of permitting UV radiation which has a high level of intensity and power in the interior volume 21 of the treatment unit 1. By way of example, this radiation can be put into effect such as to provide a quantity of energy of approximately at least 3 mJ/cm$^2$, ideally at least 3.5 mJ/cm$^2$. Similarly, by way of example, this radiation can be put into effect such as to provide an intensity of energy of approximately at least 900 μW/cm$^2$, ideally at least 950 μW/cm$^2$. These examples of radiation put into effect for a period of approximately at least 30 seconds can thus have virucide action on the air flow treated of approximately at least 99%, or even 99.99%.

According to an example of a structure relating to another variant embodiment of the invention which can be combined with the different preceding variant embodiments, the processing unit 1 comprises at least one light-emission source, or at least one set of light-emission sources 5 with a wavelength of between 100 nm and 400 nm positioned at a section of the air circulation path in the interior of the volume 21 of the unit 1 situated in the vicinity of a respective input orifice 3. This particular positioning of at least one source of emission of UV light 5 in the interior of the treatment unit 5 provides an arrangement in which the germicide or virucide effect of the radiation is applied to the flow of air as close as possible to its input in the interior of the treatment unit 1, such as to take advantage of this effect over a maximal portion of the air circulation path, in the interior of the treatment unit 1. In addition, the positioning of a source of emission of UV light 5 in the vicinity of each of the input orifices 3 of the unit 1 makes it possible to provide specific germicide/virucide treatment, i.e. which is suitable for each of the incoming air flows. According to a preferred example of a structure, a light-emission source 5 is associated with each input orifice 3 of the unit 1, such that the interior volume 21 of the treatment unit 1 is covered by the radiation of these sources of emission 5.

According to an example of a structure relating to another variant embodiment of the invention, which can be combined with the different preceding variant embodiments, the processing unit 1 is produced in the form of a cartridge 2 which has a substantially flattened arrangement, defining firstly a peripheral frame 23, and secondly two wide opposite surfaces 24, which are surrounded respectively by this peripheral frame 23, and are positioned on both sides of the cartridge 2, such that at least one of these two surfaces 24 comprises at least one output orifice 4. According to this structural example, the flattened arrangement of the cartridge 2 makes it possible to produce a processing unit 1 which has a limited spatial requirement, such that it can easily be positioned in the interior of existing ventilation, in particular at a section of a part of the air flow displacement circuit in this ventilation. This substantially flat arrangement of the cartridge 2 also permits positioning of the treatment unit 1 such as to obstruct a section of the flow of circulation of air in ventilation, such that at least part of the flow of air in this ventilation is forced to be displaced through the treatment unit 1. The positioning of the output orifice 4 of the air of the cartridge 2 at one of the two surfaces 24 also makes it possible to orient the flow of air output in a direction substantially orthogonal to the mean plane of the treatment unit 1, such that, at the output of the treatment unit 1, the air is reintroduced efficiently into the ventilation circuit. According to an example which relates to a specific feature of this structural variant, the output orifice 4 is supported by a structure which forms a wing, for example in the form of a protuberance, at the peripheral frame 23 of the cartridge 2. The output orifice 4 is thus positioned on the plane of one of the surfaces 24 of the cartridge 2, such that the flow is oriented in a direction substantially orthogonal to the mean plane of the treatment unit 1. According to an example which relates to a structural variant, the output orifice 3 is also positioned on one of the surfaces 24 of the cartridge 2, preferably on a surface different from that which supports the output orifice 4.

According to an example of a structure relating to another variant embodiment of the invention, which can be combined with the variant embodiment previously described, the cartridge 2 comprises at least one input orifice 3 positioned at one portion at least of the peripheral surface of the frame 23. The direction of the flow of air which enters the cartridge 2 is thus oriented along an axis substantially orthogonal to the axis of the direction of the flow of air output from the cartridge 2. This difference of orientation between the flow of air entering and the flow of air exiting makes it possible, within the interior volume 21 of the cartridge 2, when this volume is greater than the input 3 and output 4 orifices of the cartridge 2, to generate different turbulences in this interior volume 21, such that the germs and viruses in suspension can be present for a longer period of time in this interior volume 21, and be exposed for longer to the UV radiation of the light-emission source 5. Similarly, this difference of orientation makes it possible to slow down the circulation of the flow of air in the interior of the cartridge 2, such that the germs and viruses in suspension in this case also are exposed for longer to the UV radiation. According to a specific example of a structure, the input orifice 3 supported by the peripheral frame 23 comprises at least one grid or grooved arrangement which is configured to have a structure forming a plurality of juxtaposed baffles distributed along the input orifice 3. This grid or grooved arrangement in the form of baffles thus permits provision of a flow of air entering towards the interior of the cartridge 2, while preventing part of the UV radiation supplied by the light-emission source 5 in the interior of the cartridge 2 from being emitted towards the exterior of the treatment unit 1. By way of example of a structure, these baffles supported by the input orifice 3 have the form of one or more rows of fixed shutters which are oriented substantially parallel to one another in an arrangement similar to that of louvers.

According an example of a structure relating to another variant embodiment of the invention, which can be combined with the different preceding variant embodiments, the treatment unit 1 also comprises at least one securing interface positioned on a part of the periphery of the cartridge 2, and/or at least one interface for connection of the light-emission source 5 to a supply network. This securing interface thus permits the integration and blocking imposition of the treatment unit 1 in ventilation equipment. By way of example, this securing interface can be produced in the form of a screwing interface or clipping mechanism which permits facilitated assembly of the treatment unit 1 on the ventilation device 6, and in particular at an orifice for circulation of the flow of air in the device 6. The connection interface permits the supply of at least one of the sources of light 5 of the treatment unit 1 from a supply network on the exterior of the treatment unit, such that the operation of the treatment unit 1 does not require the presence of an on-board source of energy. By taking advantage of an exterior supply via this connection interface, the reduction of the spatial requirement of the treatment unit 1 can thus also be optimised.

According to an example of a structure relating to a construction which is an alternative to the variant embodiment previously described, the treatment unit 1 comprises at least one on-board unit for the supply of the sources of light 5 of the treatment unit 1. By way of example, this on-board unit can take the form of or more batteries incorporated in the treatment unit 1, and specifically dedicated to a source of light 5 or a set of several sources of light 5 of the treatment unit 1.

The invention also relates to a ventilation device 6, characterised in that the ventilation device 6 incorporates at least one treatment unit 1 according to the invention. The treatment unit 1 is incorporated such that the treatment unit 1 closes a section of at least part of the path of circulation of the air in the ventilation device 6. This closing of the section of this portion of the path thus makes it possible to ensure intervention of the treatment unit 1 on all of the flow of air being displaced through the said portion of the path. The treatment unit 1 forms an element which is structurally independent from the remainder of the ventilation device 6. The flow of air is displaced by one or more ventilation mechanisms specific to the ventilation device 6, with the treatment unit 1 being without any ventilation mechanism. By way of example, the ventilation device 6 is configured to generate a flow of air of approximately 834 $m^3$ per hour, such that, for application to a passenger space 7 of a public transport vehicle, all of the volume of air of the passenger space 7 can be renewed in less than 5 minutes or even during a ventilation cycle which lasts approximately 3 to 2 minutes.

It should be pointed out that, for reasons of safety, access to the treatment unit 1 in the ventilation device 6 is associated with a mechanism for stoppage of the operation of the treatment unit 1, and in particular cut-off of the supply of the different sources of light 5. Thus, handling of the treatment unit 1 is carried out without any risk to a handler. In addition, the operation of the different sources of light 5 of the treatment unit 1 is associated with a light signal in the visible spectrum, so as to warn any handler that the supply of the different sources of light 5 has not been cut off, and that handling of the treatment unit 1 is liable to constitute a danger.

According to an example of a structure relating to a variant embodiment of the invention, with the ventilation device 6 being associated with a passenger space 7 such as to provide ventilation of the air of the passenger space 7, at least one treatment unit 1 is positioned on the path of circulation of the air in the ventilation device 6, between at least one input orifice 63 and at least one output orifice 64, such that all of the air circulating in the ventilation device 6, obtained from the passenger space 7, passes through at least one treatment unit 1. According to an example of a structure, the ventilation device 6 comprises a single input orifice 63 and/or a single output orifice 64 for the flow of air, at which there is positioned a treatment unit 1 which permits treatment of all of the flow of air passing through the ventilation device 6. According to another example of a structure, the ventilation device 6 comprises a plurality of input orifices 63 and/or a plurality of output orifices 64 at each of which, at the input or output, a treatment unit 1 is positioned. According to each of these examples, all of the flow of air being displaced in the interior of the ventilation device 6 is forced to pass through at least one unit 1 according to the invention in order to be treated there.

According to another example of a structure relating to a variant embodiment of the invention which can be combined with one of the preceding variants, with the ventilation device 6 being associated with a passenger space 7 such as to ventilate the air of the passenger space 7, the ventilation device also comprises at least one input orifice 65 for air obtained from the exterior of the passenger space 7, and destined for the interior of the passenger space 7. According to this structural variant, the circuit of the flow of air in the ventilation device 6 is configured such that the air obtained from the interior of the passenger space 7 is treated by a treatment unit 1, in order to be mixed with a flow of air obtained from the exterior of the vehicle, before being ventilated towards the interior of the passenger space 7. In addition to the renewal of the air in the passenger space 7, this structural variant also makes it possible to ventilate towards the interior of the passenger space 7, which makes it possible to generate a slight excess pressure in the interior of the passenger space 7, this excess pressure being balanced in particular by a phenomenon of expulsion of air from the interior of the passenger space 7, firstly at the different junctions of elements of the passenger space 7 which are not sealed, and secondly at the moment of opening of the doors of the passenger space 7, in particular each time the vehicle stops, when it is designed for public transport.

It will be appreciated that the invention is not limited to the embodiments described and/or represented in the appended drawings. Modifications remain possible, in particular from the point of view of the composition of the various elements, or by substitution of technical equivalents, without however departing from the field of protection of the invention.

The invention claimed is:

1. An air treatment unit produced in the form of a cartridge, which is configured to be positioned on at least part of the air circulation path in ventilation equipment, said air treatment unit comprising:
    an interior volume which is associated with at least one input orifice; and
    at least one output orifice positioned at the ends of an air circulation path,
    wherein at least part of the interior surface of the volume is equipped with at least one light-emission source with a wavelength of between 100 nm and 400 nm, designed to radiate towards the interior of the volume of the air treatment unit at one section at least of the air circulation path in the interior of the volume of the air treatment unit,
    wherein the air circulation path in the interior of the volume of the air treatment unit comprises at least one baffle positioned in the interior volume, such that no ray obtained from the at least one light-emission source can pass through the at least one input orifice and/or the at least one output orifice of the air treatment unit, and
    wherein the cartridge has a substantially flattened arrangement, defining firstly a peripheral frame, and secondly two wide opposite surfaces, which are surrounded respectively by this peripheral frame, and are positioned on both sides of the cartridge, such that at least one of these two surfaces comprises at least one output orifice and that the cartridge comprises at least one input orifice positioned at one portion at least of the peripheral surface of the frame, such that the direction of the flow of air which enters the cartridge is oriented along an axis substantially orthogonal to the axis of the direction of the flow of air output from the cartridge.

2. The air treatment unit according to claim 1, wherein at least part of the interior surface of the interior volume is produced in the form of a surface which is suitable for reflection of at least part of the radiation with a wavelength of between 100 nm and 400 nm, such that this radiation converges at one section at least of the air circulation path in the interior of the interior volume of the unit.

3. The air treatment unit according to claim 1, wherein the unit comprises at least one light-emission source, or at least one set of light-emission sources with a wavelength of between 100 nm and 400 nm positioned at a section of the air circulation path in the interior of the volume of the unit situated in the vicinity of a respective input orifice.

4. The air treatment unit according to claim 1, wherein the air treatment unit also comprises at least one securing interface positioned on a part of the periphery of the cartridge, and/or at least one interface for connection of the light-emission source to a supply network.

5. A ventilation device, comprising at least one air treatment unit according to claim 1.

6. The ventilation device according to claim 5, wherein, with the ventilation device being associated with a passenger space such as to provide ventilation of the air of the passenger space, at least one air treatment unit is positioned on the path of circulation of the air in the ventilation device, between at least one input orifice and at least one output orifice, such that all of the air circulating in the ventilation device, obtained from the passenger space, passes through at least one air treatment unit.

7. The ventilation device according to claim 5, wherein, with the ventilation device being associated with a passenger space such as to ventilate the air of the passenger space, the ventilation device also comprises at least one input orifice or air obtained from the exterior of the passenger space, and destined for the interior of the passenger space.

* * * * *